United States Patent
Brommersma

(10) Patent No.: US 6,616,656 B2
(45) Date of Patent: Sep. 9, 2003

(54) TWO-ELECTRODE ENDOSCOPIC IMPLEMENT

(75) Inventor: Pieter Brommersma, Bargteheide (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 09/878,611

(22) Filed: Jun. 11, 2001

(65) Prior Publication Data

US 2001/0053910 A1 Dec. 20, 2001

(30) Foreign Application Priority Data

Jun. 16, 2000 (DE) ............................... 100 28 959

(51) Int. Cl.$^7$ ............................................ A61B 18/14
(52) U.S. Cl. ........................... 606/41; 606/46; 606/48; 606/50
(58) Field of Search ................. 606/32–52; 600/372, 600/373

(56) References Cited

U.S. PATENT DOCUMENTS

| | | | | |
|---|---|---|---|---|
| 3,920,021 A | * | 11/1975 | Hiltebrandt | 606/50 |
| 4,682,596 A | * | 7/1987 | Bales et al. | 606/50 |
| 4,966,597 A | * | 10/1990 | Cosman | 606/39 |
| 5,098,431 A | * | 3/1992 | Rydell | 606/50 |
| 5,257,635 A | * | 11/1993 | Langberg | 606/48 |
| 5,462,545 A | * | 10/1995 | Wang et al. | 606/48 |
| 5,833,688 A | * | 11/1998 | Sieben et al. | 606/41 |
| 6,217,575 B1 | * | 4/2001 | DeVore et al. | 600/373 |
| 6,379,350 B1 | * | 4/2002 | Sharkey et al. | 606/15 |
| 6,391,024 B1 | * | 5/2002 | Sun et al. | 606/34 |

OTHER PUBLICATIONS

English abstract for DE–19734506, a reference filed in an IDS on Jun. 11, 2001.
English abstract for DE–4323585, a reference filed in an IDS on Jun. 11, 2001.
WO 97/24993, Publication Date: Jul. 17, 1997, An Electrosurgical Instrument.

* cited by examiner

Primary Examiner—Lee Cohen
Assistant Examiner—Henry M. Johnson, III
(74) Attorney, Agent, or Firm—Rankin, Hill, Porter & Clark LLP

(57) ABSTRACT

An endoscopic implement including two electrodes connected to the terminals of a high frequency generator and mounted to a distal end of an elongated insertion element. An insulator is disposed between and secured to the two electrodes. One of the electrodes is mounted to a lateral surface of the insulator at a location that is laterally spaced from an axis of the insertion element. The other electrode is mounted at a distal end of the insulator.

4 Claims, 1 Drawing Sheet

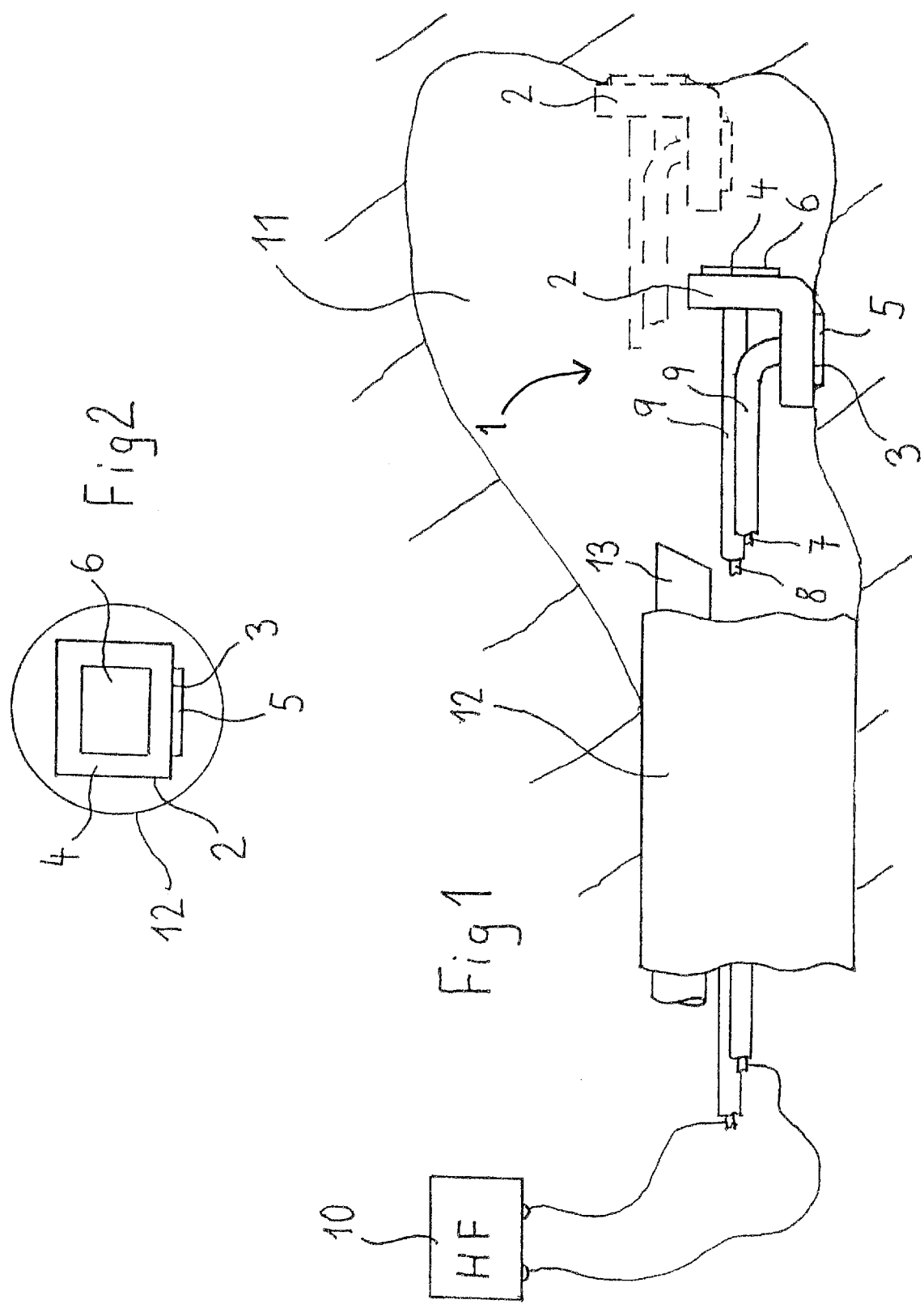

TWO-ELECTRODE ENDOSCOPIC IMPLEMENT

BACKGROUND OF THE INVENTION

1. Field of the Invention

The present invention generally relates to an endoscopic implement having two electrodes and, more particularly, to such an implement wherein each electrode is connected to a terminal of a high-frequency generator and mounted at a distal end zone of an elongated insertion element, one of the electrodes being mounted laterally to the axis of the insertion element.

2. Description of Related Art

Endoscopic implements are advanced by their elongated insertion element through the stem tube of an endoscope inserted into the body and toward a body cavity. Therein the electrodes, which are powered with high frequency current, may be used for coagulation or tissue removal. Typical applications are to the bladder, prostate or also the uterus.

As regards earlier, monoipolar procedures, the implement was fitted with only one electrode and the current was set up, through the body surface, upon contact with the tissue between the electrode and a neutral electrode. Recent bipolar implements are fitted with both electrodes at the distal end zone and, accordingly, the current is set up along the short path between them instead of through the full body.

In such an implement, as disclosed in DE 38 14 967 A1, the two electrodes are configured near each other on the surface of an insulator to carry out joint contact with the tissue. This design incurs significant drawbacks because only one of the two electrodes in contact with the tissue is able to function properly.

In an implement of this species disclosed in WO 97/24993, FIG. 9, one electrode is mounted laterally to the implement axis for the purpose of tissue contacting. The other electrode is screened by an insulator from the former electrode and mounted on the opposite side, where it is in contact with the conductive liquid filling the body cavity. A current is set up between the active electrode in contact with the tissue, over short paths of the tissue, as far as the liquid, and finally the remote neutral electrode. The insulator between the two electrodes prevents direct current flow through the liquid between the electrodes, thereby averting wasting substantial energy from the power supply.

Intrinsically, however, the use of this known implement fitted with a lateral, active electrode applies only to lateral procedures. Such an implement allows treating within a cavity only surfaces which are to its sides. Wall segments of the cavity that are situated in front of the implement, therefore, are excluded on account of geometry.

SUMMARY OF THE INVENTION

An objective of the present invention is to create an endoscopic implement that has a wider applicability and that removes the deficiencies of the devices known in the art.

In accordance with the present invention, the implement is fitted with a lateral electrode, a distally-mounted electrode, and with an insulator disposed between the lateral and distal electrode to act as a current-blocker. The invention abandons the idea that only the lateral electrode implements of the species shall be the active electrode and that the other electrode shall only serve as the neutral electrode for liquid contacting. Instead, the invention provides parity between the two electrodes, and selectively either the lateral or the distal electrode shall be the active electrode making contact with the tissue while the other electrode is then freely situated in the liquid and acts as a neutral electrode for the current return. The invention assumes that an insulator shall be an effective screen between the electrodes not only when the electrodes are mounted mutually opposite said insulator, but also when they are configured laterally and distally. When the electrodes are configured laterally and distally, the insulator shall preclude short current paths between the electrodes or, in other words, it will constrain at least the otherwise shorted current between the electrodes into detours so as to reduce power losses.

In further accordance with the present invention, the insulator has a lateral surface and an end face. The electrodes are mounted to the insulator to be mutually shielded against unwanted currents. Preferably, the electrodes are mounted centrally and directly to one of the lateral surface and the end face of the insulator.

In further accordance with the present invention, the electrodes have extended topologies or configurations. In this manner they are especially well suited to the intended purposes of coagulation and surface removal of tissue by means of the so-called vaporization method.

In further accordance with the present invention, the insulator surfaces project beyond the electrodes. When applying an electrode to the tissue surface, the rim of the insulator surface enclosing the electrode will also rest on the tissue and, in this manner, current flow between the electrodes is especially effectively blocked.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
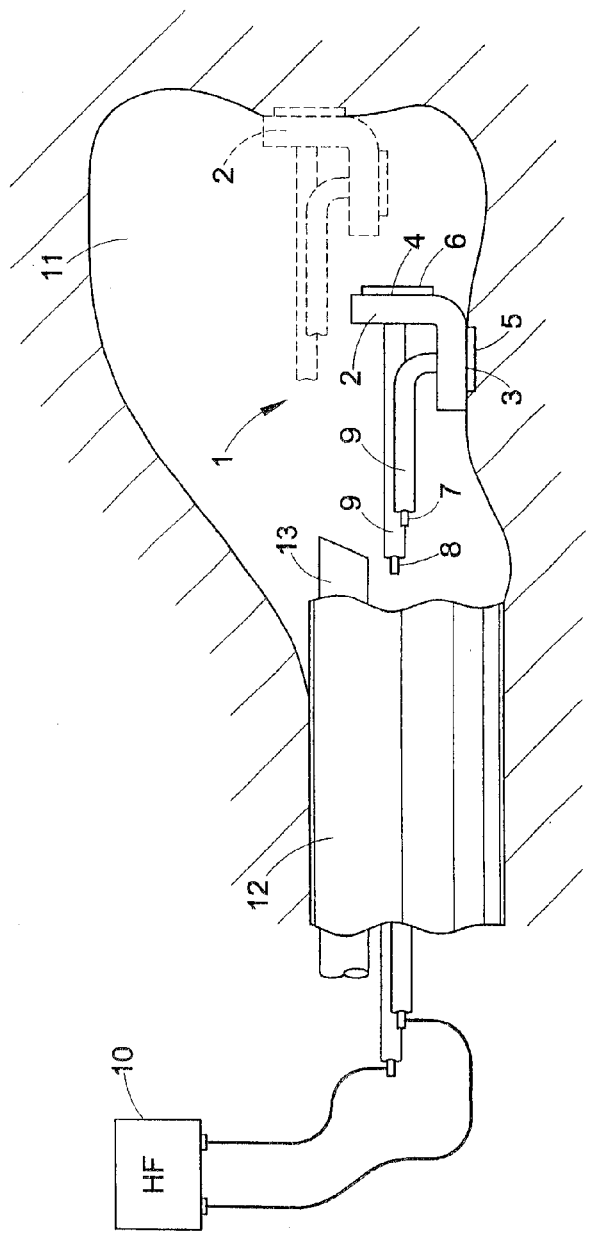
FIG. 1 is a schematic side view of an implement according to the invention disposed in a body cavity during intervention.

The implement shown in FIG. 1 comprises a straight and elongated insertion element 1 at the distal end of which is mounted an insulator 2 that, for instance, is made of ceramic. The insulator 2 subtends a planar lateral surface 3 situated laterally of the axis of the insertion element 1 and an end face 4, which is perpendicular to the axis.

Figure 2:
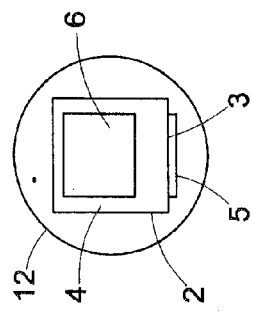
FIG. 2 is a front cross-sectional view of the implement of FIG. 1.

The implement also includes first and second electrodes 5, 6. One of the electrodes 5, 6 is mounted on the insulator lateral surface 3 and the other of the electrodes 5, 6 is mounted on the insulator end face 4. In the embodiment shown, the electrodes 5, 6 are flat plate electrodes. Their size, in each case, is smaller than that of the associated lateral surface or end face 4, respectively. As a result, as shown in particular by FIG. 2, their areas are smaller than those of the insulator 2. Accordingly, the insulator projects beyond or surrounds the electrodes 5, 6 at both the lateral surface 3 and the end face 4.

Electric leads 7, 8 passing through the insulator 2 make contact with the electrodes 5, 6 and are insulated over their length by electrical insulation 9. As shown in FIG. 1, the conductors 7, 8 are connected to the terminals of a high frequency generator 10.

FIG. 1 shows a typical application of the illustrative implement to a body cavity 11, which is shown only schematically. Illustratively, this may be the bladder or the inside of the uterus. The typical application to prostate resection in a prostate cavity may also be involved.

An endoscope, shown schematically, is emplaced from the outside and as far as into the body cavity 11. The endoscope comprises a stem tube 12 through the lumen of which the shown implement may be advanced as far as into the cavity 11. The stem tube 12 encloses an optics 13 for observation of the implement in use.

FIG. 1 represents an embodiment or mode of use wherein the implement makes contact through the lateral electrode 5 with the tissue. When the high frequency generator 10 is ON, a current is flowing from the lateral electrode 5 into the body tissue, from the surrounding surface of the body tissue into the body cavity 11 filled with conductive liquid, and through the liquid to the distal electrode 6.

As shown by FIG. 1, the current also might be shorted through the tissue between the two electrodes. In that case the current would not affect the tissue and would merely waste power. As shown by FIG. 1, such a direct current through the liquid however is blocked by the shape of the insulator 2, which constrains the otherwise short-path current into resistance-raising detours. Moreover, the large-area design of the lateral surface 3 results in a topological rest of this lateral surface against the tissue by means of the edge zones of said surface projecting beyond the electrode 5, as a result of which the short current paths through the liquid are blocked. In this manner a straight-path current between the electrodes is very effectively blocked.

FIG. 1 also shows, in dashed lines, that the implement also can be placed in contact, by means of the distal electrode 6, with the tissue at the end face of the body cavity 11. In this case the lateral electrode 5 makes free liquid contact. The current path is as discussed above but the direction of flow is reversed.

When the shown implement is rotated about its axis so that the lateral electrode 5 is situated upward, then the roof of the shown body cavity also may be treated. Accordingly the shown implement makes it feasible to treat all surface zones of the body cavity.

In the embodiment above, the insulator 2 is shown in its basic, angled shape. However this basic shape also may be closed, for instance being substantially cubical. Preferably the insulator's edges shall be rounded to avoid unintended injury to the tissue. The lateral surface 3 and the end face 4 of the insulator 2 are shown as being plane surfaces in the above embodiment. However they also may be slightly convex illustratively to allow a large-area contact with the tissue in very small cavities.

The above, preferred embodiment shows large-area electrodes 5, 6. However these electrodes may subtend only small areas, for instance being button-shaped centrally at the surface and face 3 and 4 of the insulator 2.

What is claimed is:

1. An endoscopic implement comprising an elongated insertion element defining an axis and having a first electrode and a second electrode, each of said electrodes adapted to be connected to a terminal of a high frequency generator and being mounted at a distal end zone of the elongated insertion element with an insulator being disposed between said electrodes, wherein each of said first and second electrodes has a flat, planar face, and wherein said first electrode defines a first plane that is oriented generally perpendicular to said insertion element axis while said second electrode defines a second plane that is oriented generally parallel to said insertion element axis such that when one of said first and second electrodes is in engagement with tissue the other of said first and second electrodes is configured to be spaced from the tissue so as to be freely disposed in liquid adjacent the tissue.

2. The implement as claimed in claim 1, wherein the insulator has a lateral surface (3) and a distal end face (4), and wherein said first electrode is mounted to said end face and said second electrode is mounted to the lateral surface.

3. The implement as claimed in claim 2, wherein the electrodes (5, 6) are topologically mounted on the lateral surface and end face (3, 4) of the insulator (2).

4. The implement as claimed in claim 3, wherein the lateral surface and end face (3, 4) of the insulator surround the electrodes so as to project on all sides beyond the electrodes (5, 6).

* * * * *

UNITED STATES PATENT AND TRADEMARK OFFICE
CERTIFICATE OF CORRECTION

PATENT NO.     : 6,616,656 B2
DATED          : September 9, 2003
INVENTOR(S)    : Brommersma It is certified that error appears in the above-identified patent and that said Letters Patent is hereby corrected as shown below:

Drawings,
Sheet 1 of 1, please insert the attached revised drawing sheet.

Signed and Sealed this

Twenty-fifth Day of November, 2003

JAMES E. ROGAN
*Director of the United States Patent and Trademark Office*